(12) United States Patent
Smulders et al.

(10) Patent No.: US 6,792,360 B2
(45) Date of Patent: Sep. 14, 2004

(54) HARMONIC ACTIVITY LOCATOR

(75) Inventors: Adrianus J. Smulders, San Diego, CA (US); Jim J. Wei, San Diego, CA (US); Johannes I. Boerhout, San Diego, CA (US)

(73) Assignee: SKF Condition Monitoring, Inc., San Diego, CA (US)

( * ) Notice: Subject to any disclaimer, the term of this patent is extended or adjusted under 35 U.S.C. 154(b) by 0 days.

(21) Appl. No.: 10/313,228

(22) Filed: Dec. 4, 2002

(65) Prior Publication Data

US 2003/0130810 A1 Jul. 10, 2003

Related U.S. Application Data

(60) Provisional application No. 60/336,810, filed on Dec. 4, 2001.

(51) Int. Cl.[7] .............................................. G06F 19/00
(52) U.S. Cl. ........................................ 702/35; 73/579
(58) Field of Search .............................. 702/33–36, 39, 702/54, 56, 73–78, 106, 113–115, 182–185, 189, 60; 73/579, 587, 862.08; 704/207; 123/406.38

(56) References Cited

U.S. PATENT DOCUMENTS

| | | | | |
|---|---|---|---|---|
| 4,956,999 A | * | 9/1990 | Bohannan et al. | ............ 73/587 |
| 4,989,158 A | | 1/1991 | Sloane | ........................ 700/280 |
| 5,086,775 A | | 2/1992 | Parker et al. | ............... 600/453 |
| 5,201,292 A | * | 4/1993 | Grajski et al. | ......... 123/406.38 |
| 5,214,960 A | * | 6/1993 | Tsuboi | ......................... 73/579 |
| 5,216,921 A | * | 6/1993 | Tsuboi | ......................... 73/579 |
| 5,251,151 A | | 10/1993 | Demjanenko et al. | ........ 702/56 |
| 5,800,331 A | * | 9/1998 | Song | .............................. 494/7 |
| 5,864,058 A | | 1/1999 | Chen | ....................... 73/152.47 |
| 6,144,924 A | * | 11/2000 | Dowling et al. | .............. 702/60 |
| 6,484,109 B1 | * | 11/2002 | Lofall | ......................... 702/56 |
| 6,546,814 B1 | * | 4/2003 | Choe et al. | .............. 73/862.08 |
| 6,587,816 B1 | * | 7/2003 | Chazan et al. | .............. 704/207 |
| 6,681,633 B2 | * | 1/2004 | Schultz et al. | ................ 73/587 |

FOREIGN PATENT DOCUMENTS

| | | |
|---|---|---|
| WO | WO 00/55583 | 9/2000 |
| WO | WO 02/38914 A2 | 5/2002 |

* cited by examiner

*Primary Examiner*—Marc S. Hoff
(74) *Attorney, Agent, or Firm*—Knobbe Martens Olson & Bear LLP

(57) ABSTRACT

Systems and methods for identifying the presence of a defect in vibrating machinery. An exemplary method comprises analysis of frequency spectrum vibration data of the machine. The method comprises deriving a harmonic activity index based on estimates of the energy associated with the frequency spectrum and the energy associated with the defect's harmonic series. The method may comprise deriving a value K by estimating a value M indicative of the energy of the defect's harmonic series and dividing M by the number of spectral lines corresponding to the defect's harmonic series. The method may further comprise deriving a value R by estimating a value Q indicative of the energy in the frequency spectrum data and dividing Q by the number of spectral lines of the frequency spectrum data. The method further comprises deriving the harmonic activity index based on the estimated K and R. Related systems for executing the methods are also disclosed.

34 Claims, 5 Drawing Sheets

US 6,792,360 B2

HARMONIC ACTIVITY LOCATOR

RELATED APPLICATIONS

This patent application claims priority under 35 U.S.C. §119(e) to, and hereby incorporates herein by reference, U.S. Provisional Patent Application 60/336,810, titled "HARMONIC ACTIVITY LOCATOR," filed Dec. 4, 2001.

BACKGROUND OF THE INVENTION

1. Field of the Invention

The invention generally relates to vibration analysis for monitoring the condition of machinery. More specifically, the invention is directed to systems and methods for detecting the development or presence of defects, or other impactive forces, in the components of a machine by analysis of the frequency spectrum of the vibrations of the machine.

2. Description of the Related Art

It is common for industrial and commercial facilities to operate a large number of machines concurrently, many of which may cooperate in a large interdependent process or system. Despite increasingly efficient maintenance programs, at any time some percentage of the machines develop defects that are likely to lead to machine failure. For example, machines having moving parts (e.g., bearings) experience constant friction that results in wear. It is known that bearing failures are a major cause of motor faults. Bearing damage due to wear may not be apparent, however, absent gross damage or failure of the motor because the bearing's wear site is most likely concealed in the motor's assembled state.

Consequently, the use of machine condition monitoring systems has become essential to preventive maintenance of industrial machinery in order to avoid down time or catastrophic failure of machines. Unscheduled plant shutdowns can result in considerable financial losses. Failure of high performance machinery can lead to fatal injury and processing system backup. Typical benefits from a preventive maintenance program include longer periods between machinery shutdowns, evaluation of the condition of machine components without resorting to costly and/or destructive disassembly for visual inspection, and prolonging the machinery's operational life by taking corrective action when developing faults are identified early.

Rotating and reciprocating components of a machine produce vibrations having a wide range of frequencies. The vibration of a machine or a machine component may be characterized as the sum of amplitudes (or "peaks") at a "fundamental frequency" (or "natural frequency") and its harmonic frequencies. As used here the term "harmonic frequency" refers to a frequency that is a multiple of the fundamental frequency. Typically, the harmonic components (i.e., peak and frequency values) of a vibration are plotted as vertical lines on a diagram of amplitude versus frequency. This diagram is commonly referred to as a "frequency spectrum," "spectral diagram," or "spectrum plot."

The frequencies and associated peaks of the vibrations of a specific machine collectively make up the "frequency spectrum" for the machine, also known as the machine's "vibration signature." A machine's vibration signature varies with, for example, the design, manufacture, application, and wear of its components. The machine's normal operating conditions determine the amplitude of steady (or "normal") vibration. It is a common practice to obtain a reference frequency spectrum when the machine is known to be in good condition for comparison against future measurements of the machine's frequency spectrum. Such comparison aids in detecting changes in the condition of the machine or its subcomponents. Hence, analysis of a machine's vibration signature provides valuable insights into the condition of the machine.

The machine's frequency spectrum typically shows one or more discrete frequencies around which the vibration energy concentrates. Since the vibration characteristics of individual components of a machine are usually known or can be estimated, distinct frequencies of the frequency spectrum may be associated with specific machine components. That is, it is possible to relate each peak of the machine's frequency spectrum to a specific component of the machine. For example, a peak at a given frequency may be associated with the rotational speed of a particular motor. The machine's frequency spectrum serves to indicate that the motor might be the cause of the machine's vibrations. If the motor is causing excessive vibrations, changing either the motor or its speed of operation might avoid deleterious resonance (i.e., excessive and damaging vibrations).

Typically, as a component of a machine wears down or develops a defect, the vibration level of the component and the machine increases. Hence, many machine faults have a noticeable effect on the size and shape of the peaks of the machine's frequency spectrum. If a component defect produces a known frequency, the peak at that frequency increases as the fault progresses. The frequency thus arising is termed a "fault frequency" or "defect frequency." Usually the defect also produces vibrations of frequencies that are multiples of the fault frequency (i.e., harmonics), in addition to the fault frequency. For example, the meshing of gears produces several harmonics, and the peaks of the higher harmonics indicate the quality of the gear mesh. Thus, changes in peaks of vibrations may indicate developing defects, and the health of a particular component may be analyzed by considering the peaks at its fundamental and/or harmonic frequencies.

The term "component defect" as used here refers in general to any undesirable machine or component vibration condition ("fault") that is detected by a vibration sensor and may be represented with a spectral harmonic series. The term "defect" is to be understood as a developing or fully developed fault. For example, a defect may be simply the wear of a gear tooth, or a flat spot on a bearing.

There are several methods of identifying a component defect by analysis of a machine's frequency spectrum. In one method, detection of a component defect is made by identifying amplitude peaks at the vibration frequency, or frequencies, of the component defect. However, in practical applications, the true component defect frequency may not be the same as that given by the component manufacturer or that which is predicted by on-site measurements. Additionally, although a nominal value for the defect frequency is readily calculable, measurement errors and the combination of the vibration signals from different components and other sources result in a signal-to-noise ratio at the defect frequency that may be insufficient for accurate analysis.

Another method of detecting component defects is to use a frequency search band around the nominal component defect frequency, the search band having a bandwidth of a certain percentage of its center frequency. The highest peak within the search band is identified as the component defect signal. This method is often referred to as constant percentage bandwidth (CPB) analysis.

However, CPB has its shortcomings and, consequently, in some cases it is not satisfactory. Since the bandwidth of the search band is a percentage of the center frequency, the higher the center frequency the wider the search band. At the high frequencies the search band grows very wide and includes more peaks within it. Often, for high order harmonic search bands, the strongest peak within the band may not be harmonically related. This results in non-harmonic peaks being identified as component defect harmonics, which leads to inaccurate results.

Thus, there is a continuing need in the industry for systems and methods that define current condition of the machine and predict safe operating life accurately relying on the fewest measurements and incurring the least cost.

SUMMARY OF THE INVENTION

The methods and systems of the invention have several aspects, no single one of which is solely responsible for its desirable attributes. Without limiting the scope of this invention as expressed by the claims which follow, its more prominent features will now be discussed briefly.

The systems and methods of the invention generally concern devices and techniques for detection of component defects, or other impactive phenomena, in machinery. In one embodiment, the invention provides a method of deriving a parameter ("$I_{HAL}$") whose value is correlated with the presence of component defects in a machine. $I_{HAL}$ is at least partly dependent on the features of the machine's frequency spectrum. It has been empirically determined that $I_{HAL}$ values exceeding a certain threshold indicate the presence of component defects at the harmonic series under consideration. Hence, one use of $I_{HAL}$ is for monitoring the condition of a machine and issuing a warning or alarm condition when $I_{HAL}$ exceeds a predetermined threshold.

In one embodiment the invention concerns a method of identifying machine component defects. The method comprises receiving a frequency spectrum vibration data set for the machine. The method further comprises estimating the most likely component defect fundamental frequency and its harmonics, and estimating the spectral energy related to these frequencies. The method further comprises estimating the energy associated with the frequency spectrum of the machine. The method further comprises relating the spectral energy associated with the component defect harmonics to the total energy in the entire frequency spectrum to produce a unitless value that may be used as an index representative of the "harmonicness" of the frequency spectrum of the machine. This unitless value is referred to here as the harmonic activity locator index or $I_{HAL}$. In some applications, $I_{HAL}$ may be used to differentiate between vibration measurements indicative of component problems and vibration measurements unrelated to component defects.

Another aspect of the invention concerns a method of identifying a component defect in a machine subject to vibrations. The method comprises estimating from frequency domain vibration data a value R indicative of the spectral energy of said vibrations. The method further comprises estimating from said data a value K indicative of the spectral energy associated with said component defect. The method further comprises deriving a harmonic activity index based at least in part on the estimated values K and R.

Another aspect of the invention is directed to a method of differentiating between vibration measurements indicative of the presence of a component defect in a machine and vibration measurements unrelated to the component defect. The method comprises receiving a frequency spectrum associated with said machine. The method further comprises estimating a component defect fundamental frequency and harmonic frequencies and associated amplitudes. The method further comprises estimating a value K indicative of the total energy associated with said fundamental and harmonic frequencies. The method further comprises estimating a value R indicative of the total energy associated with said spectrum. The method further comprises deriving a value $I_{HAL}$ based at least in part on the estimated values K and R. The method further comprises determining based at least in part on $I_{HAL}$ and the fundamental frequency of the component defect whether the vibrations of the machine are produced by the component defect.

In one embodiment, the invention relates to a system for monitoring the condition of a machine by analysis of the machine's vibrations. The system comprises a data storage module that receives and stores data indicative of amplitudes of vibrations said machine at selected frequencies. The system further comprises a data analyzer module, in communication with said data storage module, that derives a harmonic activity index. The data analyzer comprises computer instructions operative for estimating from said data a value R indicative of the spectral energy of said vibrations and value K indicative of the spectral energy associated with said component defect. The data analyzer also comprises computer instructions operative for deriving said harmonic activity index based at least in part on the estimated K and R.

BRIEF DESCRIPTION OF THE DRAWINGS

The above and other aspects, features, and advantages of the invention will be better understood by referring to the following detailed description, which should be read in conjunction with the accompanying drawings, in which.

DETAILED DESCRIPTION OF CERTAIN EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
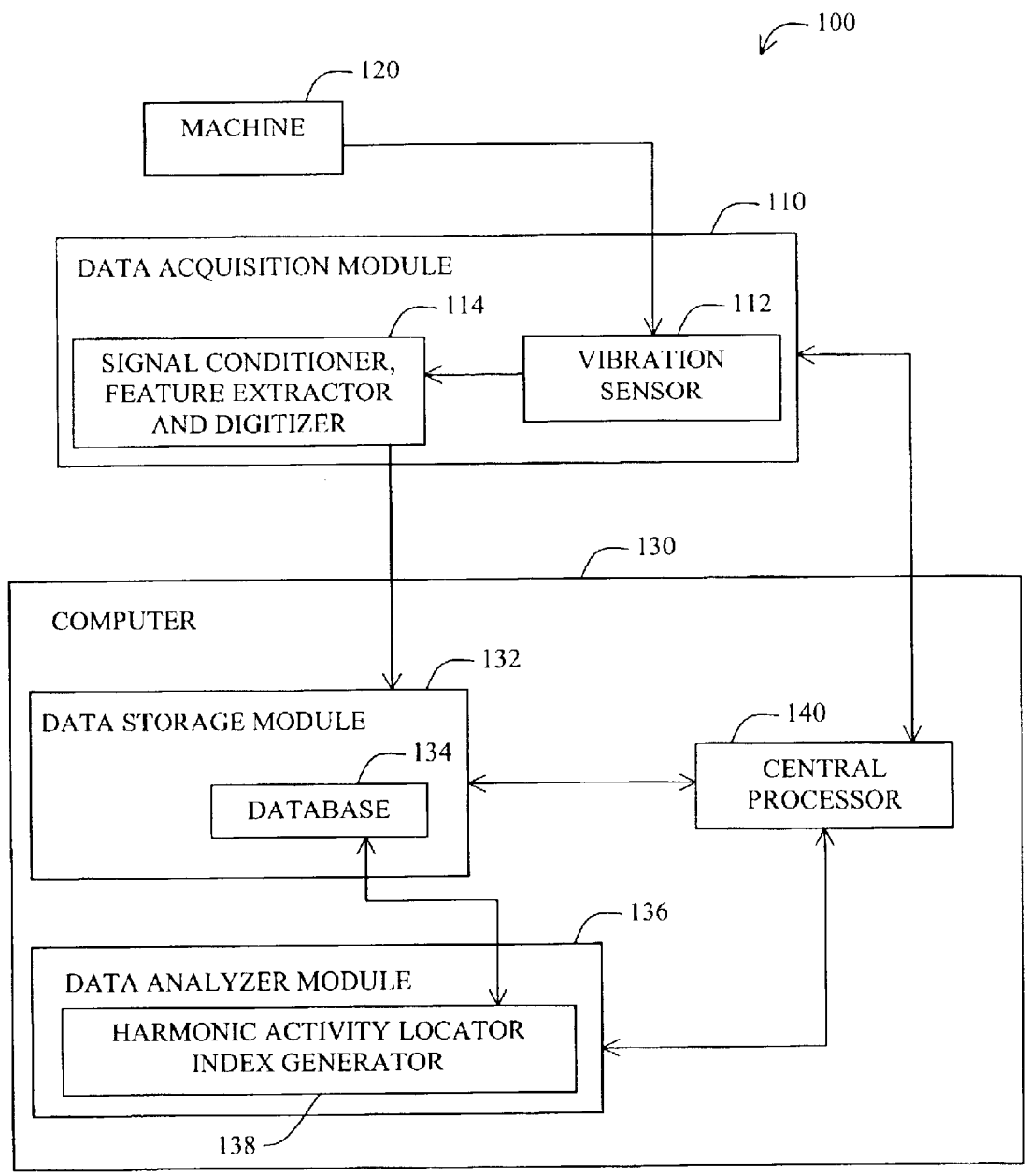
FIG. 1 is a block diagram of a system for detection of a machine component defect in accordance with one embodiment of the invention.

FIG. 1 illustrates a system 100 for detection of a machine component defect in accordance with one embodiment of the invention. The system 100 consists of a data acquisition module 110 in communication with a computer 130. The data acquisition module 110 is coupled to a machine 120 for detecting vibrations of the machine 120. The data acquisition module 110 transmits the vibration data to the computer 130, which analyzes the vibration data to detect a defect in a component (not shown) of the machine 120.

The accurate analysis of machine vibration is dependent on the ability to deliver a true vibration signal to the data analyzer module 136. In some embodiments, the data acquisition module 110 comprises a vibration sensor 112 that is coupled to the machine 120 to detect vibrations of the machine 120. The vibration sensor 112 is typically configured to measure one or more of the three basic parameters of vibrations, namely displacement (i.e., amplitude), velocity, and acceleration. Typically, the vibration sensor 112 converts the motion of the vibrating machine 120 into electrical signals. These vibration sensing devices and their use are well known by persons of ordinary skill in the relevant technology.

The data acquisition module 110 may also comprise a signal conditioner, feature extractor and digitizer 114. The vibration sensor 112 transmits the vibration signals to a signal conditioner and digitizer 114 that consists of electrical circuits for conditioning (e.g., amplifying and/or filtering), extracting features, and digitizing the vibrations signals. Device 114 may be configured to perform analog post processing to enhance certain features of the signal before digitizing. For example, the device 114 may use acceleration enveloping to enhance repetitive signals. The electrical circuits of the signal conditioner, feature extractor and digitizer 114 are well known in the relevant technology.

The computer 130 may be any computing device that is configured to receive, store, and analyze the vibration data transmitted to the computer 130 by the data acquisition module 110. The computer 130 may be, for example, a server computer, a personal computer, a portable computer, a handheld computer, or a personal digital assistant, etc.

The computer 130 comprises a data storage module 132 in communication with a data analyzer module 136. The data storage module 132 may be any nonvolatile memory storage device, such as a hard drive, magnetic tape, etc. The data storage module 132 has one or more databases 134 for storing the data provided by the signal conditioner and digitizer 114. The database 134 may be a data storage structure in the form of a list, table, or relational database, as is well known in the relevant technology.

The computer 130 also comprises a central processor 140 that is in communication with the data storage module 132 and the data analyzer module 136. The central processor 140 coordinates communications between the data analyzer module 136 and the data storage module 132, and generally aids in the processing of data.

The data analyzer module 136 consists of one or more software/hardware or firmware components for analyzing the vibration data of the machine 120 to identify a defect in a component of the machine 120. The data analyzer module 136 comprises a harmonic activity locator index generator 138 ("index generator 138") that analyzes the vibration data (i.e., the frequency spectrum of the machine 120) to produce a value indicative of the presence of a component defect. This value is referred to here as the harmonic activity locator index (or "$I_{HAL}$")

It should be understood that while the description of the invention generally refers to identifying component "defects," the systems and methods disclosed here may also be used to identify any "impactive signal" acting on a machine 120. An impactive signal may arise, for example, from forces external to the machine 120 that act randomly or periodically upon it. The operation and use of the harmonic activity locator index generator 138 will be described in further detail below with reference to FIGS. 2, 3A, 3B, and 4.

It should be understood that the structure of the system 100 as depicted in FIG. 1 is only exemplary of one system in accordance with the invention. More particularly, it will be apparent to a person of ordinary skill in the relevant technology that the data acquisition module 110 and the computer 130 need not be two separate devices. That is, in some embodiments the data acquisition module 110 module may be integral with (i.e., be a part of, or located in) the computer 130. Conversely, it is not necessary that any of the components of the system 100 be commonly housed or in each other's vicinity. For example, the vibration sensor 112 may be attached to the machine 120 and remotely located from the signal conditioner and digitizer 114. In such a case, the vibration sensor 112 may transmit the vibration data to the signal conditioner and digitizer 114 via wireless communication, for example. Similarly, the data storage module 132, data analyzer module 136, and central processor 140 may communicate via wireless or nonwireless channels, and may be located remotely from each other. Moreover, it will be readily recognized by the person of ordinary skill in the relevant technology that the system 100 may comprehend multiple vibration sensors 112 on multiple machines 120 providing vibration data to one or more computers 130.

A typical use of the system 100 will now be described. The vibration sensor 112 collects vibration data from a machine 120. During collection of the vibration data, the machine 120 is preferably running under normal operating conditions, but data collection may also take place at other times, e.g., when testing the machine after manufacturing it or refurbishing it. The vibration sensor 112 transmits the vibration data, usually in the form of electrical signals, to the signal conditioner and digitizer 114. The signal conditioner and digitizer 114 may, for example, amplify the electrical signals and filter out noise. Preferably, the signal conditioner and digitizer 114 also digitizes the electrical signals for communication to the computer 130. In some embodiments, the signal conditioner and digitizer 114 transforms the vibration data from the time domain (i.e., vibration amplitude versus time) to the frequency domain (i.e., vibration amplitude versus frequency) to produce a frequency spectrum of the vibrations of the machine 120. The signal conditioner and digitizer 114 may use a Fast Fourier Transform ("FFT") technique, for example, to extract the amplitude and frequency features of the vibration data obtained by the vibration sensor 112.

The computer 130 receives the vibration data from the data acquisition module 110 for further processing. The computer 130 stores the vibration data, e.g., the time domain response or a frequency spectrum, in the database 134. The data analyzer module 136, in cooperation with the central processor 140, retrieves the vibration data from the data storage module 132 for analysis by the index generator 138. The index generator 138 evaluates the frequency spectrum of the machine 120 and produces a value $I_{HAL}$ indicative of the condition of the machine 120 or any one of its subcomponents. The data analyzer module 136 may evaluate the $I_{HAL}$ with reference to a predetermined threshold and, based on this evaluation, determine whether to issue a component defect alarm, for example.

Figure 2:
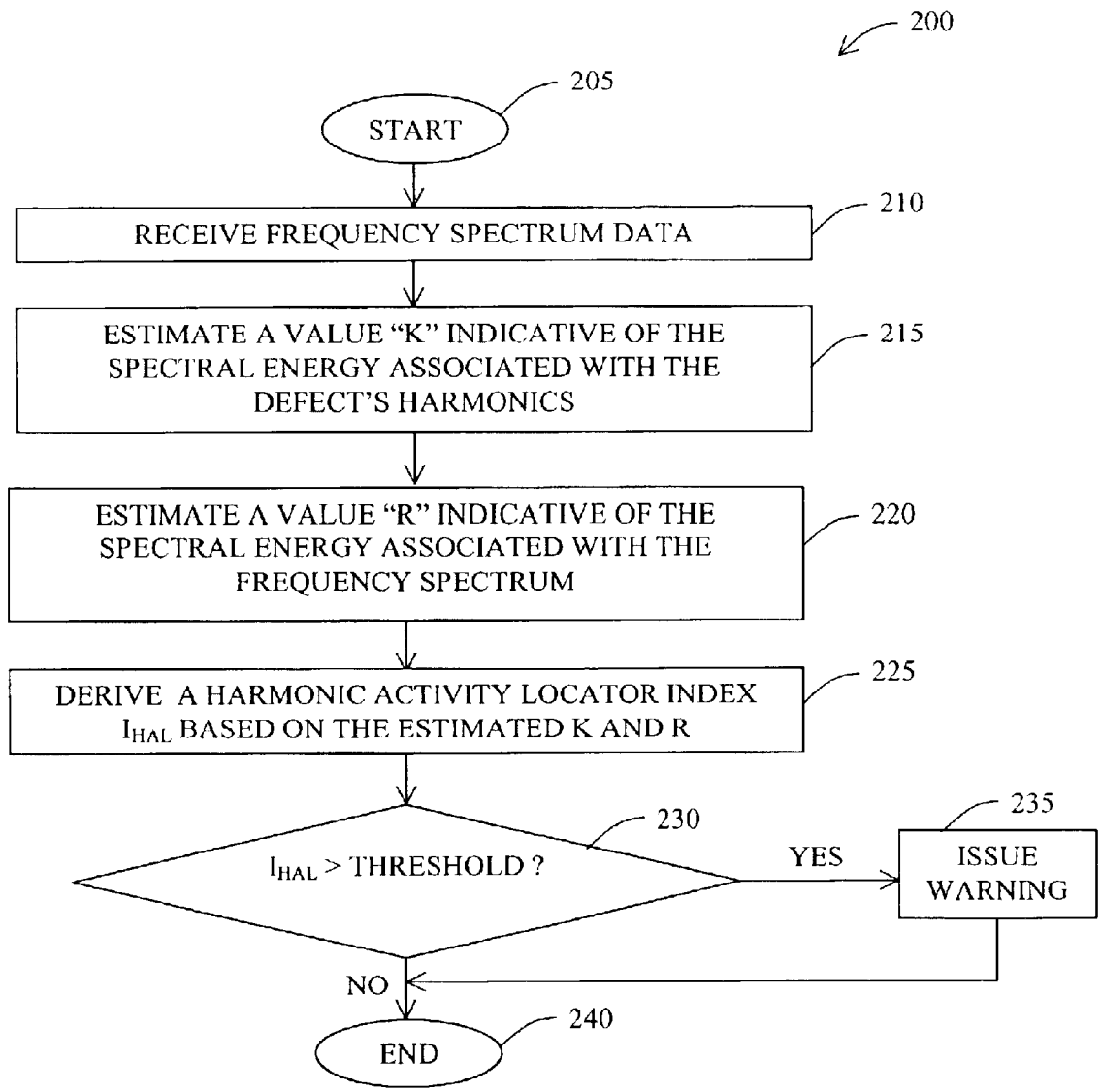
FIG. 2 is a high-level flowchart of a method of detecting a machine component defect according to one embodiment of the invention. The method may be used in conjunction with the system shown in FIG. 1.

FIG. 2 illustrates a process 200, which may be used in conjunction with the system 100, of identifying component defects in a machine 120 by analyzing the frequency spectrum of the machine 120. The process 200 starts at a state 205 after the data acquisition module 110 communicates the vibration data to the computer 100, which stores the vibration data, preferably in the form of vibration amplitudes and corresponding frequency values, in the data storage module 132. At a state 210, the data analyzer module 136 receives the frequency spectrum data. The process 200 continues at a state 215, wherein the index generator 138 estimates a value "K" indicative of spectral energy associated with the defect's harmonic vibration frequencies, which include the fundamental frequency and at least some higher harmonics available in the frequency spectrum data. An exemplary manner of estimating K is described below with reference to FIGS. 3A, 3B, and 4. The process 200 proceeds to a state 220 where the index generator 138 estimates a value "R" indicative of the total spectral energy associated with all, or most of all, the spectral lines of the frequency spectrum received by the data analyzer module 136. The system 100 may estimate R by employing the methods described in FIGS. 3A and 3B, for example.

At a state 225, the index generator 138 derives $I_{HAL}$ from a formula defined at least in part by K and R. For example, in a preferred embodiment, $I_{HAL}$ is proportional to the ratio of K to R, i.e., $I_{HAL} = t*K \div R$, wherein t is a scaling constant usually set at unity. In another embodiment, $I_{HAL}$ is proportional to the ratio of K to the difference between R and K, i.e., $I_{HAL} = tK \div (R-K)$.

After determination of $I_{HAL}$, the process 200 may continue at a decision state 230 where the computer 130 determines the relationship between $I_{HAL}$ and a predetermined threshold. As will be further discussed below, it has been empirically determined that $I_{HAL}$ values greater than about 2 are substantially correlated with component defects or other significant impactive forces acting on the machine 120. Hence, for example, if $I_{HAL}$ is greater than 2, the computer 130 may issue a warning at a state 235, and the process 200 then ends at a state 240. If, however, $I_{HAL}$ is not sufficiently high to indicate a component defect, the process 200 ends at the state 240 without issuing a warning.

It will be apparent to a person of ordinary skill in the relevant technology that the different actions described with reference to the process 200 need not be performed in the same order as shown in FIG. 2. Additionally, of course, in some embodiments it is not necessary to perform all of the actions described. For example, after deriving $I_{HAL}$ at the state 225 the process 200 may end at the state 240, rather than proceeding to the decision state 230. In other embodiments of the process 200, more states or sub-states may be included.

Figure 3A:
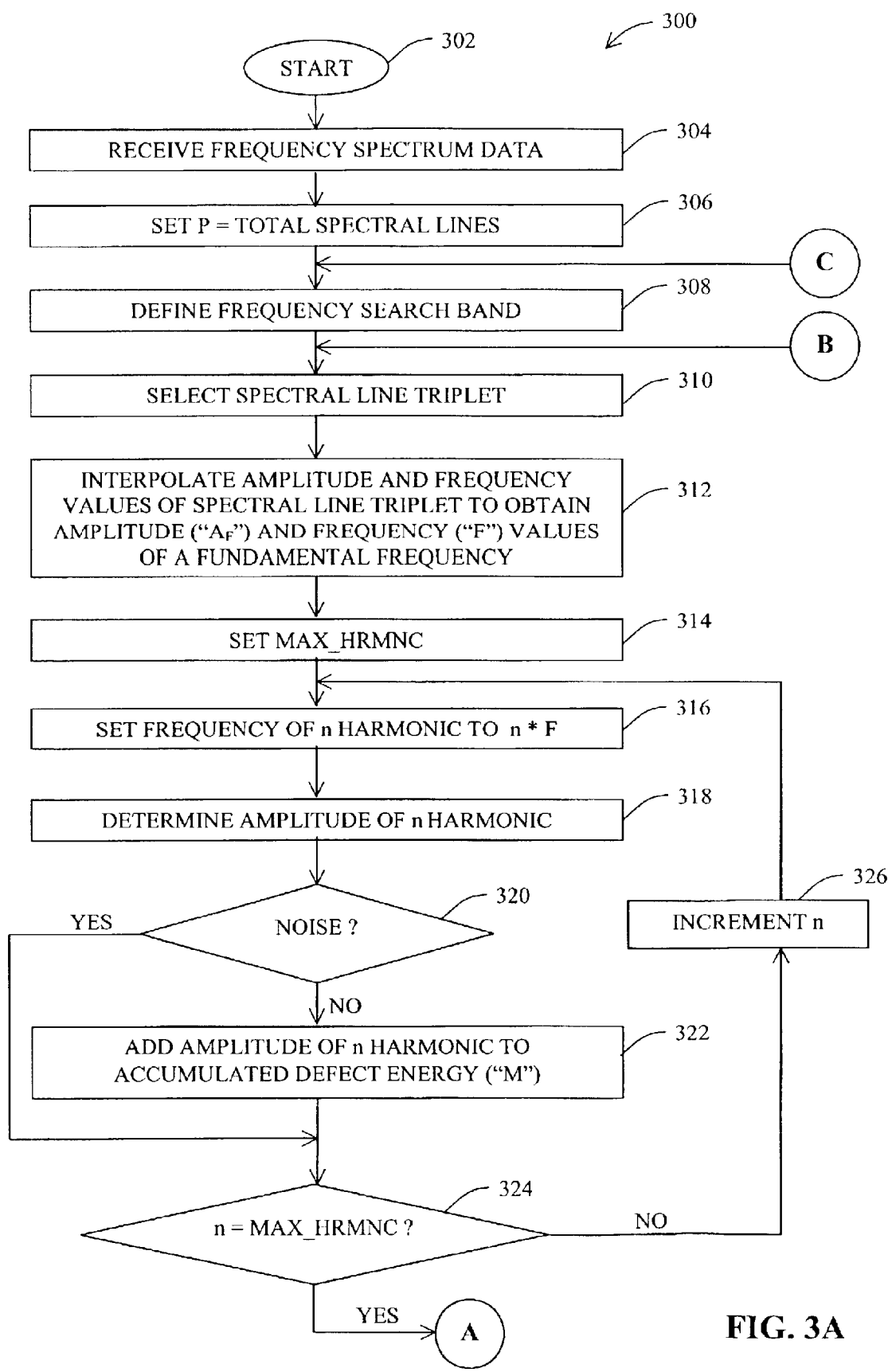
FIG. 3 is a flowchart of a method of detecting a machine component defect corresponding to yet another embodiment of the invention. The method may be employed in conjunction with the system shown in FIG. 1.
Figure 3B:
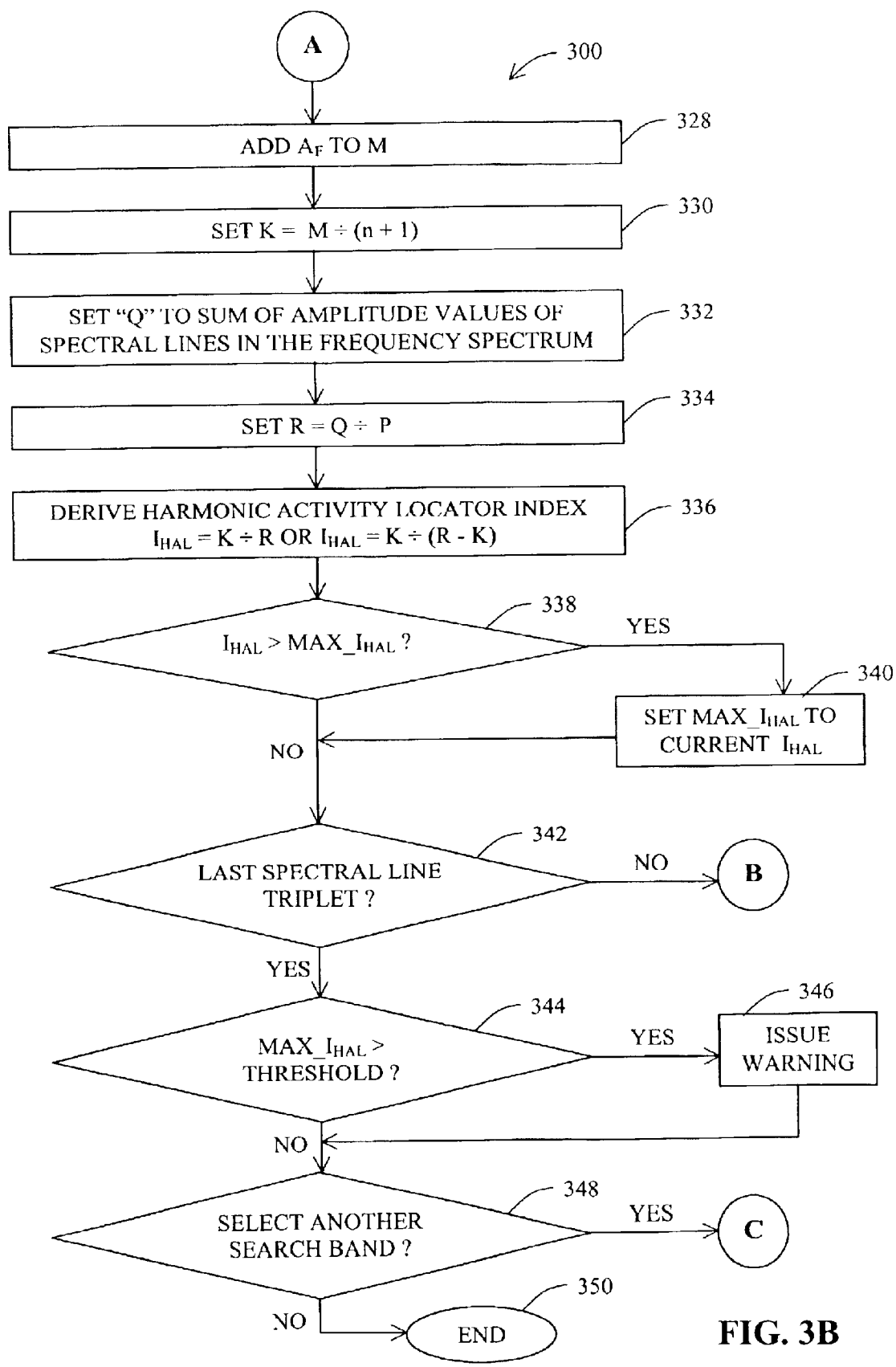

FIGS. 3A and 3B depict a process 300 of identifying component defects in accordance with yet another embodiment of the invention. This method may be used in conjunction with the system 100 shown in FIG. 1. The method 300 starts at a state 302 after, for example, the data acquisition module 110 transmits the vibration data of the machine 120 to the computer 130. At a state 304, the data analyzer module 136 receives the frequency spectrum data by, for example, making requests of the data storage module 132 via the central processor 140. In one embodiment, the frequency spectrum data comprises amplitude and corresponding frequency values for the vibrations sensed by the vibration sensor 112.

At a state 306 of the process 300, the index generator 138 determines the total number "P" of spectral lines in the frequency spectrum under consideration. The process 300 next proceeds to a state 308, wherein the index generator 138 defines a frequency search band which corresponds to a likely location of the fundamental frequency of a component defect. A nominal value for the fundamental frequency of the component defect is typically provided by the manufacturer of the component. In a preferred embodiment, the search band is defined by specifying a lowest and a highest frequency, respectively below and above of the defect's expected fundamental frequency, in between which the index generator 138 evaluates peaks to empirically estimate the defect's fundamental frequency as measured by the vibration sensor 112. The manufacturer's nominal value for the fundamental frequency of a component's defect may be used as the expected fundamental frequency. In another preferred embodiment, the index generator 138 receives input specifying the bandwidth of the search band as a percentage of the expected defect's fundamental frequency. For example, useful results may be obtained by specifying the bandwidth of the search window to be about ±2% of the defect's fundamental frequency.

As previously mentioned, in a conventional method of determining the peak of the defect's fundamental frequency, the spectral line in the frequency spectrum closest to the expected defect's fundamental frequency is chosen. However, the accuracy of the conventional method is largely influenced by the frequency resolution of the vibration measurement. Hence, the conventional method results in an error that is directly proportional to the number of harmonics included in the evaluation, because the estimated energy contribution of the $n^{th}$ harmonic generates an error as large as n*E (E being the error, i.e., the difference, between the estimated and true fundamental frequencies of the component defect). Consequently, in the methods of the present invention it is preferable to obtain a more accurate estimate of the defect's fundamental frequency, as is described below.

The process 300 continues at a state 310, where the index generator 138 selects a triplet 400 (see FIG. 4) of spectral lines for evaluation in determining the amplitude at the defect's fundamental frequency. The index generator 138 selects within the search band a spectral line triplet 400 having a center amplitude (e.g., $F_i$ of FIG. 4) with two adjacent smaller amplitudes (e.g., $F_{i-1}$ and $F_{i+1}$ of FIG. 4).

Figure 4:
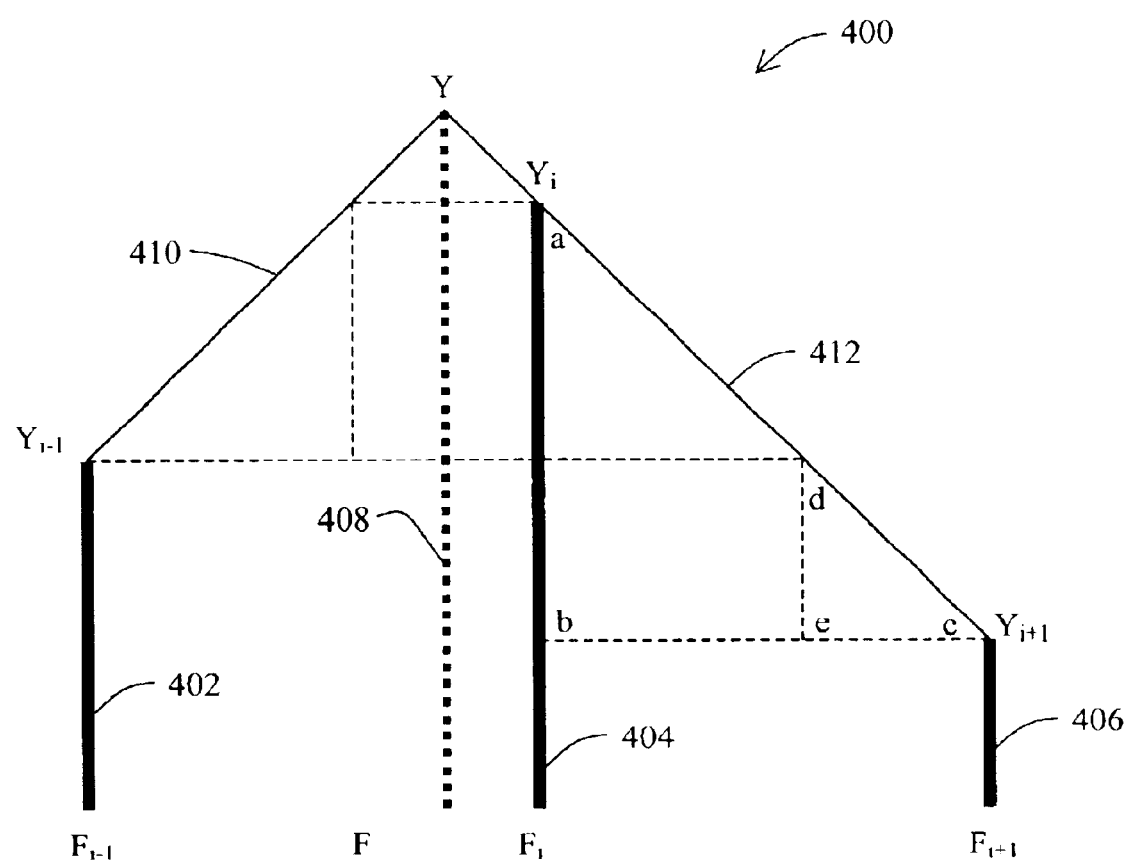
FIG. 4 is a diagram of a triplet of spectral lines as may be used to obtain the fundamental frequency of a component defect. The defect's fundamental frequency may be used in conjunction with the methods of FIG. 2 or FIG. 3.

The index generator 138, at a state 312 of the process 300, estimates a value for the defect's fundamental frequency and a corresponding amplitude by interpolation of the values associated with the spectral line triplet selected above. Interpolation is useful in cases in which the fundamental frequency of the component defect falls between spectral lines, which typically occurs where sensed amplitude information is transformed into frequency data as a series of discrete frequency values. Any suitable interpolation method may be used including, for example, linear interpolation. FIG. 4, described below, provides an exemplary technique for interpolating the amplitude and frequency values of the spectral line triplet 400 in order to derive an estimate of the defect's fundamental frequency and corresponding amplitude.

The process 300 continues at a state 314 wherein the index generator 138 sets or reads a variable MAX_HRMNC, which is indicative of the highest order harmonic to be included in the analysis. MAX_HRMNC may vary widely and may, for example, be set to values from 3–25. This means that in some embodiments, the index generator 138 includes at least 25 harmonics of the fundamental frequency in the analysis. The inclusion of about 4, 5, 6, 7, 8, 9, or 10 harmonics of the fundamental frequency of the component defect has been found to give useful results. The process 300 next moves to a state 316 where the index generator 138 approximates the frequency of the n order harmonic as a multiple of n times the defect's fundamental frequency F, e.g., $F_2=2*F$ with n=2.

The frequencies of the harmonics determined above do not necessarily correspond exactly to spectral lines of the frequency spectrum evaluated by the data analyzer module 136. Consequently, at a state 318, the index generator 138 estimates a value for the amplitude corresponding to the derived harmonic frequency. The index generator 138 approximates the amplitude of any given harmonic by interpolating between the neighboring spectral lines in the vicinity of the estimated harmonic frequency, and which are characterized by having a center spectral line having a peak greater than its two immediately adjacent neighbors. For example, the third harmonic 3*F may fall between two adjacent spectral lines which have magnitude values $Y_j$ and $Y_{j+1}$ respectively. The index generator 138 estimates the amplitude of the third harmonic by interpolating between the values $Y_j$ and $Y_{j+1}$.

It is possible that the frequency spectrum includes additional harmonic patterns or other frequencies with strong amplitudes that approximately coincide with one or more frequencies in the harmonic series estimated by the index generator 138 but which are unrelated to the component defect. Of course, if the index generator 138 includes the unrelated values in determining $I_{HAL}$, the value of $I_{HAL}$ may be significantly skewed and, thus, lead to erroneous conclusions. Consequently, at a decision state 320, the index generator 138 may detect and reject peaks unrelated to the defect's harmonics as "noise."

Several known noise reduction approaches may be used. In one embodiment, the index generator 138 reduces noise by excluding from the total spectral energy associated with the harmonics of the component defect any peak that is more than about 10 times greater or less than about 10 times lower than the amplitude at the defect's fundamental frequency. Of course, it should be apparent to a person of ordinary skill in the relevant technology that the parameter "10" used here is not specifically necessary and may be optimized for a particular application.

If at the decision state 320 the index generator 138 determines that the estimated amplitude of the spectral line at the harmonic under consideration is likely noise, the process proceeds to a decision state 324. However, if the index generator 138 determines that the amplitude is not noise, then at a step 322 the index generator 138 add the estimated amplitude of the current order harmonic to M, which the aggregation or sum of all the amplitudes of the harmonics (excluding the fundamental frequency) of the component defect.

The process 300 continues at the decision state 324, where the index generator 138 determines whether n=MAX_HRMNC. If n is not equal to MAX_HRMNC this indicates that there remains higher order harmonics for evaluation by the index generator 138. In such a case, the process moves to a state 326 where the index generator 138 increments the value of n, meaning that the index generator 138 selects the next defect harmonic for evaluation. Next, the process 300 proceeds to a state 316. If, however, the index generator 138 has evaluated all the harmonics to be considered in determining $I_{HAL}$, the process 300 continues at a state 328 via off-page indicator A (see FIG. 3B).

The index generator 138 increments M by adding to it the amplitude $A_F$ of the defect's fundamental frequency at a state 328. Hence, M represents the total accumulated energy of the defect's harmonics, including the energy of the defect's fundamental frequency. Continuing to a state 330 of the process 300, the index generator 138 sets a value "K" indicative of the total spectral energy of the defect's harmonics by dividing M by the total number of peaks in the harmonic series of the defect, namely n+1. That is, K=M÷N, where N=n+1.

The process 300 proceeds at a state 332, where the index generator 138 determines a value Q by adding all of the amplitudes of the peaks in the frequency spectrum received by the data analyzer module 136. Of course, in some embodiments, it may be desirable to ignore certain peak values meeting some predetermined criteria. That is, it is not necessary that every single one of the peaks in the frequency spectrum be included in Q. In one embodiment of the invention, however, in determining Q the index generator 138 includes substantially all of the peaks of the frequency spectrum of the machine 120.

Next, at a state 334, the index generator 138 derives a value "R" indicative of the total spectral energy in the frequency spectrum received by the data analyzer module 136. In the embodiment shown, the index generator 138 sets R to be directly proportional to the ratio of Q to P, wherein P is the total number of peaks included in determining Q. In other embodiments, R may be scaled by a predetermined coefficient depending on the specific application; hence, R may be derived from a relationship given by R=s*Q÷P, where s is a predetermined scaling constant.

Continuing at a state 336 of the process 300, the index generator 138 calculates $I_{HAL}$ with a formula defined at least in part by K and R. For example, the index generator 138 may derive $I_{HAL}$ by dividing the value K, which is indicative of the spectral energy associated with the harmonics of the component defect, by R, which is indicative of the total spectral energy in the frequency spectrum of the machine 120. In other embodiments of the invention, the index generator 138 may derive $I_{HAL}$ as the ratio of K to the difference between R and K, that is, $I_{HAL}=K÷(R-K)$. It has been determined empirically that both of these relationships provide useful results in identifying component defects, or other impactive forces acting on a machine 120, by analysis of frequency spectrum data collected from the machine 120.

As has been previously stated, $I_{HAL}$ provides a useful indication of the condition of a machine 120. Through experimentation on vibration data sets collected from machines in operation, it has been noticed that $I_{HAL}$ values greater than about 2, for example, appear to be well correlated with defects in bearings, or other machine components.

The use of $I_{HAL}$ is advantageous since, unlike in conventional methods that require setting and maintaining regular absolute sensor alarm values, the disclosed methods embodying the invention may be based on deriving only a single parameter, i.e., $I_{HAL}$. The higher $I_{HAL}$ becomes, the more likely that the harmonic pattern evaluated corresponds to a component defect. Accordingly, $I_{HAL}$ may be used to indicate a level of confidence as to whether a significant failure mode is present in a machine 120. Moreover, a person of ordinary skill in the relevant technology will recognize that use of $I_{HAL}$ reduces or completely eliminates the need to set an absolute sensor alarm value that is unique for each measurement type and location. This is significantly advantageous in industrial applications, for example, where thousands of alarm values must be set and maintained.

A person of ordinary skill in the relevant technology will readily recognize that although the discussion here generally has focused on monitoring machine condition to identify component defects, $I_{HAL}$ may also be used to detect the presence of other "impactive" or "pulsating" phenomena acting upon the machine 120 and which generates a harmonic series in the frequency spectrum data of the machine 120. For example, if the system 100 finds that $I_{HAL}$ exceeds a predetermined threshold at a certain frequency and its harmonics, that frequency may be compared against expected fundamental frequencies of component defects associated with the machine 120. If the frequency associated with the high $I_{HAL}$ does not correspond to any of the expected fault frequencies, it may be assumed that a pulsating or impactive phenomenon (possible external to the machine 120) is acting upon the machine 120 and causing the vibrations, rather than a component defect being the source of the vibrations.

In some embodiments, the process 300 may end at a state 350 after the index generator 138 produces $I_{HAL}$ at step 336. However, in other embodiments (as illustrated in FIGS. 3A and 3B) the process 300 may include additional states. Hence, after the index generator 138 determines $I_{HAL}$, the computer 130 may determine at a state 338 of the process 300 whether the $I_{HAL}$ computed on the basis of the spectral line triplet 400 selected at state 310 is greater than the greatest $I_{HAL}$ previously determined, namely MAX_$I_{HAL}$. If that is the case, the process 300 continues to a state 340 where the computer 130 sets a variable MAX_$I_{HAL}$ to the current $I_{HAL}$, and then moves to the decision state 342. Also, if $I_{HAL}$ is not greater than MAX_$I_{HAL}$, the process 300 continues at the decision block 342, where the computer 130 determines whether the index generator 138 has evaluated all the spectral line triplets in the frequency search band defined at state 308. If there remains triplets for analysis by the index generator 138, the process 300 continues (via off-page indicator B) at the state 310 where the index generator 138 selects another spectral line triplet in the same manner as already described above. If there are no spectral line triplets 400 remaining for analysis by the index generator 138, the process 300 proceeds to a decision state 344.

In some embodiments of the invention, the computer 130 may be configured to determine whether the maximum $I_{HAL}$ value derived from analysis of all the triplets in a given search band exceeds a predetermined threshold. Hence, for example, at the decision state 344 the computer 130 may evaluate whether MAX_$I_{HAL}$ is greater than a certain threshold, which may be empirically determined for a given type of machine 120 or its subcomponents. For example, the threshold may be set to 2. Then, if MAX_$I_{HAL}$ is greater than 2, the computer 130 may issue a warning at a state 346 of the process 300.

After issuing of the warning, or if MAX_$I_{HAL}$ is less than the threshold, the process 300 may continue at a decision state 348. Of course, in some embodiments the process 300 may proceed to end state 350 and terminate after the decision state 344. This would be the case where, for example, only one frequency search band of interest is evaluated.

However, in some embodiments it may be practical and desirable to consider multiple search bands for analysis of larger parts (even including the whole) of the frequency spectrum evaluated by the data analyzer module 136. In such an embodiment, it is possible to mine databases of vibration data to detect possible component faults or other sources of machine vibration. For example, using the methods disclosed here in data mining on a database storing machine vibration data revealed multiple bearing problems without requiring user intervention or detailed knowledge of component defect characteristics. In data mining, the index generator 138 evaluates an $I_{HAL}$ value for each spectral line triplet 400 (see FIG. 4) found in the frequency spectrum of the machine 120. If $I_{HAL}$ exceeds a predetermined threshold, this could indicate that there is an anomalous vibration source acting upon the machine 120; the vibration source being an identifiable component defect or some other impactive or pulsating phenomena acting upon the machine 120.

In another embodiment, the data analyzer module 136 analyzes trends in the condition of the machine 120 by data mining historical vibration data of the machine 120. By way of illustration, in some cases the data acquisition module 110 periodically obtains vibration data from the machine 120 over a period of 12 to 24 months, for example, and stores that data in the data storage module 132. Each time the data acquisition module 110 obtains vibration data, it stores a frequency spectrum for the machine 120 and associates the frequency spectrum with a specific time stamp, e.g., month, week, day, hour, etc. The data analyzer module 136 computes $I_{HAL}$ values for each time-stamped frequency spectrum stored in the data storage module 132 and produces a trend of the $I_{HAL}$ values over the 12 to 24 month period. It has been observed that $I_{HAL}$ values for components of a machine without significant defects will remain below a preset $I_{HAL}$ value threshold over the observation period. However, $I_{HAL}$ values for components of a machine with developing defects will over time exhibit a trend upward toward the predetermined threshold. Thus, the index generator 138 may use $I_{HAL}$ values in machine vibration analysis for extracting trends from vibration data acquired over a significantly long period of time, e.g., days, weeks, months, or years.

The person of ordinary skill in the relevant technology will readily recognize that the methods disclosed here may be used profitably to provide diagnostic functions in machine condition monitoring software or firmware. Consequently, the computer 130 may be configured to determine at the decision state 348 of the process 300 whether another frequency search band should be selected. If that is the case, the process 300 returns to step 308 of FIG. 3A via the off-page indicator C. Otherwise, the process 300 ends at the state 350.

Of course, as it will be apparent to a person of ordinary skill in the relevant technology and has been stated above, the process 300 need not include all of the states depicted in FIGS. 3A and 3B. Additionally, in some embodiments, any of the functions of process 300 may be combined and performed in a single state, or conversely, may be subdivided and executed in additional states not shown in FIGS. 3A and 3B. Finally, the person of ordinary skill in the relevant technology will recognize that one or more of the functions described above may be performed by devices or modules other than those specifically mentioned. For example, the data analyzer module 136 may perform some or all of the functions described above as being performed by the signal conditioner and digitizer 114.

As discussed above with reference to state 312 of the process 300 illustrated in FIGS. 3A and 3B, in some embodiments of the invention the index generator 138 interpolates amplitude and frequency values of a triplet of spectral lines in order to determine the most likely location of the fundamental frequency of a component defect. FIG. 4 provides a method for performing interpolation of spectral line triplets. FIG. 4 depicts a triplet 400 of spectral lines 402, 404, and 406 selected by the index generator 138 to estimate the defect's fundamental frequency. Spectral lines 402, 404, and 406 have frequencies of $F_{i-1}$, $F_i$, $F_{i+1}$, and amplitudes of $Y_{i-1}$, $Y_i$, $Y_{i+1}$, respectively. The frequency spectrum may be approximated by straight lines 410 and 412, which are intercepted by the three spectral lines 402, 404, and 406. The thin dashed lines are present in the figure only for aiding in understanding the geometric relationships used to interpolate the spectral line values according to the technique disclosed here. The estimated defect frequency is F and is shown by the dashed spectral line 408. As in FIG. 4, this exemplary case is for F less than $F_i$.

FIG. 4 shows that the triangle having vertices a, b, c is similar to the triangle having vertices d, e, and c. Thus, it follows that $$\frac{Y_i - Y_{i+1}}{Y_{i-1} - Y_{i+1}} = \frac{F_{i+1} - F_i}{2(F_i - F)} \quad (1)$$

Hence, for $F<F_i$:

$$F = F_i + \frac{1}{2} \times \frac{Y_{i+1} - Y_{i-1}}{Y_i - Y_{i+1}} \times (F_{i+1} - F_i) \quad (2)$$

and for $F>F_i$:

$$F = F_i + \frac{1}{2} \times \frac{Y_{i+1} - Y_{i-1}}{Y_i - Y_{i-1}} \times (F_{i+1} - F_i) \quad (3)$$

The value F of the defect's fundamental frequency thus obtained is more accurate than simply assuming that the defect's fundamental frequency is given by the strongest line near the expected defect's fundamental frequency in the frequency search band. Additionally, it should be noted that by using this interpolation technique the defect's estimated fundamental frequency will coincide with the central spectral line of the triplet 400, namely $F_i$, when the neighboring lines, $F_{i-1}$ and $F_{i+1}$, have equal amplitudes.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The scope of the invention is indicated by the appended claims rather than by the foregoing description. All changes which come within the meaning and range of equivalency of the claims are to be embraced within their scope.

What is claimed is:

1. A method of differentiating between vibration measurements indicative of the presence of a component defect in a machine and vibration measurements unrelated to the component defect, the method comprising:

receiving a frequency spectrum associated with said machine;

estimating a component defect fundamental frequency and harmonic frequencies and associated amplitudes;

estimating a value K indicative of the total energy associated with said fundamental and harmonic frequencies;

estimating a value R indicative of the total energy associated with said spectrum;

deriving a value $I_{HAL}$ based at least in part on the estimated values K and R; and determining based at least in part on $I_{HAL}$ and the fundamental frequency of the component defect whether the vibrations of the machine are produced by the component defect.

2. The method of claim 1, wherein estimating a value R comprises obtaining a sum Q comprising the sum of all of the amplitudes corresponding to the spectral lines in said spectrum.

3. The method of claim 2, wherein estimating a value R further comprises dividing Q by the total number of spectral lines P in said spectrum.

4. The method of claim 3, wherein deriving $I_{HAL}$ comprises dividing K by R.

5. The method of claim 3, wherein deriving $I_{HAL}$ comprises dividing K by the difference between K and R.

6. The method of claim 1, wherein estimating a component defect fundamental frequency comprises interpolating values associated with contiguous spectral lines.

7. The method of claim 6, wherein interpolating values comprises selecting a triplet of spectral lines, wherein an amplitude of a middle line of said triplet of spectral lines is greater than an amplitude of other spectral lines of said triplet of spectral lines.

8. The method of claim 1, wherein estimating a value K comprises obtaining a sum M comprising the sum of all of the amplitudes associated with the fundamental and harmonic frequencies of said component defect.

9. The method of claim 8, wherein estimating a value K further comprises dividing M by the number of harmonics N, including the fundamental frequency, associated with the component defect.

10. The method of claim 1, wherein receiving a frequency spectrum comprises receiving data indicative of amplitudes and frequencies of vibrations of said machine.

11. The method of claim 1, wherein deriving $I_{HAL}$ comprises dividing K by R.

12. The method of claim 1, wherein deriving $I_{HAL}$ comprises dividing K by the difference between K and R.

13. A method of evaluating a frequency domain spectrum of vibration data comprising:

defining a first fundamental frequency;

defining a series of harmonics of said first fundamental frequency;

summing a first set of amplitudes associated with said first fundamental frequency and at least some of said harmonics to produce a value K;

summing a second set of amplitudes to produce a value R;

calculating a value indicative of the presence of a component defect based at least in part on said first and second sums.

14. The method of claim 13, further comprising defining a second fundamental frequency, and repeating said harmonic defining, summing, and calculating acts using said second fundamental frequency.

15. The method of claim 14, further comprising repeatedly defining a series of additional fundamental frequencies and repeating said harmonic defining, summing, and calculating acts using each of said additional fundamental frequencies so as to produce a corresponding series of values.

16. The method of claim 15, wherein defining each of said fundamental frequencies comprises searching for a spectral line triplet within at least one search band in said frequency domain spectrum, said spectral line triplet having a central spectral line amplitude larger than the amplitude of either spectral line adjacent to said central spectral line amplitude.

17. The method of claim 16, further comprising searching within a plurality of search bands.

18. The method of claim 17, further comprising performing an exhaustive search throughout said frequency domain spectrum for said spectral line triplets.

19. The method of claim 13, further comprising comparing said value to a threshold.

20. The method of claim 13, wherein defining a first fundamental frequency comprises interpolating an amplitude between a pair of spectral lines of said frequency domain spectrum.

21. The method of claim 13, wherein defining a first fundamental frequency comprises searching for a spectral line triplet within a search band in said frequency domain spectrum, said spectral line triplet having a central spectral line amplitude larger than the amplitude of either spectral line adjacent to said central spectral line amplitude.

22. A method of identifying the presence of a component defect in a machine subject to vibrations, the method comprising:
- estimating from frequency domain vibration data a value R indicative of the spectral energy of said vibrations;
- estimating from said frequency domain vibration data a value K indicative of harmonically related spectral energy associated with said component defect;
- deriving a harmonic activity index based at least in part on the estimated values K and R; and
- determining the presence of said component defect based at least in part on the value of said harmonic activity index.

23. The method of claim 22, wherein estimating R comprises evaluating the total number of spectral lines of said frequency domain vibration data.

24. The method of claim 23, wherein estimating R comprises dividing a sum of all the amplitudes of said spectral lines by said total number of spectral lines.

25. The method of claim 24, wherein estimating K comprises adding amplitudes of a plurality of spectral lines that are harmonically related, and wherein estimating K further comprises dividing the result of said adding by the number of spectral lines in said plurality of spectral lines that are harmonically related.

26. The method of claim 25, wherein deriving said index comprises evaluating a ratio that is based at least in part on dividing K by R.

27. The method of claim 26, further comprising issuing a warning if the index is greater than 2.

28. The method of claim 25, wherein deriving said index comprises evaluating a ratio that is based at least in part on dividing K by the difference between R and K.

29. The method of claim 22, wherein estimating K comprises adding amplitudes of a plurality of spectral lines that are harmonically related.

30. A system for identifying the presence of a component defect in a machine subject to vibrations, the system comprising:
- a data storage module that receives and stores data indicative of amplitudes of vibrations of said machine at selected frequencies;
- a data analyzer module, in communication with said data storage module, that derives a harmonic activity index, wherein said data analyzer comprises computer instructions operative for:
  - estimating from said data a value R indicative of the spectral energy of said vibrations;
  - estimating from said data a value K indicative of the spectral energy associated with said component defect;
  - deriving said harmonic activity index based at least in part on the estimated values K and R; and
  - determining the presence of said component defect based at least in part on the value of said harmonic activity index.

31. The system of claim 30, wherein said computer instructions for deriving said index comprises computer instructions for dividing K by R.

32. The system of claim 30, wherein said computer instructions for deriving said index comprises computer instructions for dividing K by a difference between R and K.

33. The system of claim 30, wherein estimating K is based at least in part on adding a plurality of amplitudes corresponding to a harmonic series of a fundamental frequency of said component defect.

34. A system for identifying the presence of a component defect in a machine subject to vibrations, the method comprising:
- means for receiving data indicative of amplitudes and corresponding frequencies of vibrations of said machine;
- means for estimating from said data a value R indicative of the spectral energy of said vibrations;
- means for estimating from said data a value K indicative of the spectral energy associated with said component defect, wherein estimating K is based at least in part on adding a plurality of amplitudes corresponding to a harmonic series of the fundamental frequency of said component defect
- means for deriving a harmonic activity index based at least in part on the estimated values K and R; and
- means for determining the presence of said component defect based at least in part on the value of said harmonic activity index.

* * * * *